(12) United States Patent
Henry et al.

(10) Patent No.: US 6,770,707 B2
(45) Date of Patent: Aug. 3, 2004

(54) RADICALY POLYMERISABLE COMPOSITIONS CONTAINING MONOFUNCTIONAL MONOMERS, RESINS AND OPHTHALMIC ARTICLES OBTAINED FROM THEM, NEW MONOFUNCTIONAL MONOMERS

(75) Inventors: David Henry, Morigny-Champigny (FR); Cécile Lecrivain, Fontenay-sous-Bois (FR)

(73) Assignee: Corning Incorporated, Corning, NY (US)

( * ) Notice: Subject to any disclaimer, the term of this patent is extended or adjusted under 35 U.S.C. 154(b) by 427 days.

(21) Appl. No.: 09/871,030

(22) Filed: May 31, 2001

(65) Prior Publication Data

US 2002/0032304 A1 Mar. 14, 2002

(30) Foreign Application Priority Data

May 31, 2000 (FR) ............................................ 00 06988

(51) Int. Cl.$^7$ .............................................. C08L 83/00
(52) U.S. Cl. ......................... 524/588; 528/38; 526/279; 526/301; 526/302; 526/328; 525/474; 544/71; 524/110
(58) Field of Search ............................. 528/38; 526/279, 526/474, 301, 302, 328; 524/588, 110; 544/71

(56) References Cited

U.S. PATENT DOCUMENTS

| 5,237,090 A | 8/1993 | Swarup et al. |
| 5,349,035 A | 9/1994 | Brand et al. |
| 5,380,779 A * | 1/1995 | D'Haese |
| 5,691,405 A | 11/1997 | Hutter |
| 5,973,039 A | 10/1999 | Florent et al. |

FOREIGN PATENT DOCUMENTS

| EP | 471 972 | 2/1992 |
| WO | WO 93/06184 | 4/1993 |
| WO | WO 96/34030 | 10/1996 |
| WO | WO 98/50443 | 11/1998 |
| WO | WO 00/19246 | 4/2000 |

OTHER PUBLICATIONS

Database Chemabs, Chemical Abstracts Service, Columbus, Ohio, US: JP 09 143210.
Database Chemabs, Chemical Abstracts Service, Columbus, Ohio, US: JP 11 171851.
Database Chemabs, Chemical Abstracts Service, Columbus, Ohio, US: JP 01 087606.
Database Chemabs, Chemical Abstracts Service, Columbus, Ohio, US: JP 2000 63765.
Database Chemabs, Chemical Abstracts Service, Columbus, Ohio, US: JP 2000 212154.
S. Dai et al.: Macromolecules, vol. 33, No. 19, 2000, pp. 7021–7028.
L. Guo et al., Macromol. Chem. Phys., vol. 199, No. 6, 1998, pp. 1175–1185.
K. R. Olesen et al., Progress in Organic Coatings, vol. 35, No. 1–4, 1999, pp. 161–170.
V. Tirtaatmadja et al., Macromolecules, vol. 30, No. 11, 1997, pp. 3271–3282.

* cited by examiner

*Primary Examiner*—Kuo-Liang Peng
(74) *Attorney, Agent, or Firm*—Siwen Chen; Timothy M. Schaerle

(57) ABSTRACT

Disclosed are radically polymerisable compositions which contain at least one monofunctional monomer and at least one difunctional monomer; resins which are obtainable by radical copolymerisation of said compositions, it being possible for the resins to be photochromic or not; articles, notably ophthalmic articles, which are constituted totally or in part of such resins; and new monofunctional monomers.

45 Claims, No Drawings

RADICALY POLYMERISABLE COMPOSITIONS CONTAINING MONOFUNCTIONAL MONOMERS, RESINS AND OPHTHALMIC ARTICLES OBTAINED FROM THEM, NEW MONOFUNCTIONAL MONOMERS

The object of the present invention is:
radically polymerisable compositions which contain at least one monofunctional monomer with at least one difunctional monomer;
resins which are obtainable by radical copolymerisation of said compositions; it being possible for the resins to be photochromic or not;
articles, notably ophthalmic articles, which are constituted totally or in part of such resins
new monofunctional monomers.

The manufacture of a plastic ophthalmic lens is a difficult exercise insofar as it is required that the structure of said lens be free from optical constraints and obviously possesses satisfactory mechanical properties. In order to attain this result, it is necessary to perfectly master the copolymerisation reactions implemented during the preparation of said lens. It is necessary in any case to avoid attaining the gel point of the reaction system too rapidly since, in the hypothesis of "local over-cross-linking", strings and other optical faults inexorably appear. This problem is a real problem insofar as the basic monomers known hitherto are generally symmetrical difunctional monomers.

Furthermore, within the context of the manufacture of photochromic ophthalmic lenses, either by radical polymerisation of compositions which contain at least one photochromic colorant, or by later diffusion of such colorants within the polymerised matrices, it is necessary that the structure of said lens possesses, in addition to the optical qualities set forth supra, a pronounced aptitude to favour the expression of the photochromic properties of said colorants which intervene; and this without notably altering its mechanical properties.

Obtaining an acceptable compromise—optical properties, even photochromic/mechanical properties—is not an easy thing.

Hitherto, the Applicant and his competitors are still working on the improvement of this compromise.

Photochromic transparent organic materials which have good photochromic properties are described in U.S. Pat. No. 5,973,039. They are based on a tetraethoxylated bisphenol A dimethacrylate homopolymer and contain suitable photochromic colorants. The polymerisation is carried out in the presence of a suitable radical polymerisation initiator. The optical quality of these materials does however reveal to be insufficient for ophthalmic applications.

U.S. Pat. No. 5,349,035 proposes, in order to minimise, even prevent optical constraints, to combine at least one other monomer, notably of styrene, with a dimethacrylate type monomer (and notably with that set forth supra), and to carry out the copolymerisation in the presence of an effective amount of a chain transfer agent. The matrix obtained is however not suitable for expressing the photochromic properties of photochromic colorants. Said matrix notably has fading kinetics which are much too slow.

Furthermore, in the application WO-A-98 50443, organic materials have been described which are photochromic or not, which are improved, and which are based on at least two different types of difunctional monomers.

The Applicant presently proposes using monofunctional (styrenic) monomers as comonomers in radically polymerisable compositions. Said monofunctional monomers, with suitable partners, can improve the copolymerisation in question and confer flexibility to the copolymer resulting from said copolymerisation. Copolymers of this type constitute a novel material which is very interesting, and which possesses improved optical and optionally photochromic properties.

According to its first object, the present invention thus relates to radically polymerisable compositions which contains specific radically copolymerisable monofunctional monomers. Said specific monofunctional monomers are of formula (I) below

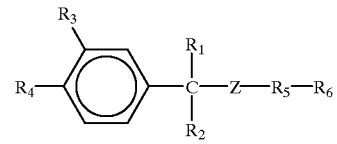

in which:
$R_1$ and $R_2$, which are identical or different, independently are hydrogen or an alkyl radical, which is linear or branched, advantageously linear, and comprises 1 to 4 carbon atoms; and particularly advantageously correspond to a methyl group;
$R_3$ and $R_4$, which are different, independently are one hydrogen and the other an alkenyl radical comprising 2 to 6 carbon atoms, advantageously 2 to 4 carbon atoms, and particularly advantageously an isopropenyl radical;
Z represents a carbamate function (—NH—CO—O—), a thiocarbamate function (—NH—CO—S—), a urea function (—NH—CO—NR$_7$, with $R_7$ which represents a hydrogen or a linear, branched or cyclic alkyl group which comprises 1 to 6 carbon atoms) or an oxazolidone function

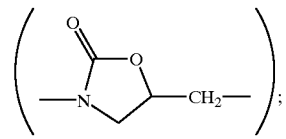

$R_5$ is selected from the group comprising:
alkylene oxide radicals and polyalkylene oxide chains of formula:

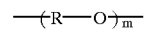

in which the R groups, which are identical or different when $m \geq 2$, are alkylene radicals, which are linear or branched, and which comprise 2 to 5 carbon atoms, and m is an integer, such that the total number of carbon atoms of said alkylene oxide radicals and polyalkylene oxide chains be between 2 and 112;
ester radicals and polyester chains of formula

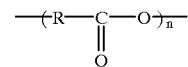

in which the R groups, which are identical or different when $n \geq 2$, are alkylene radicals, which are linear or branched, and which comprise 2 to 5 carbon atoms, and n is an integer, such that the total number of carbon atoms of said ester radicals and polyester chains be between 2 and 168;

siloxane radicals and polysiloxane chains of formula

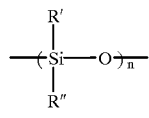

in which the R' groups and the R" groups, which are independently identical or different when n≧2, are alkyl radicals which comprise 1 or 2 carbon atoms, and n is an integer between 1 and 18;

carbonate radicals and polycarbonate chains of formula

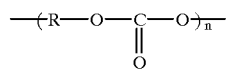

in which the R groups, which are identical or different when n≧2, are alkylene radicals, which are linear or branched, and which comprise 1 to 5 carbon atoms, and n is an integer between 1 and 21; and $R_6$ is an alkyl radical or an aryl radical.

$R_3$ or $R_4$, which is an alkenyl radical, advantageously an isopropenyl radical, constitutes the functional group of the (monofunctional) monomers. In formula (I), $R_3$ advantageously represents an isopropenyl radical (whereas $R_4$ represents hydrogen).

$R_5$ constitutes the group of said monofunctional monomers which confers flexibility to the final copolymer. $R_6$ is the terminal group of the chain. The nature of said terminal group is not a determining factor. It is advantageously a linear, cyclic or branched alkyl group which comprises 1 to 9 carbon atoms (preferably 1 to 4 carbon atoms) or an aryl group selected from optionally substituted phenyl and naphthyl groups. In formula (I), $R_5$ advantageously represents an alkylene oxide radical or a polyalkylene oxide chain. Particularly preferably, $R_5$ is selected from:

an ethylene oxide radical, a polyethylene oxide chain, a propylene oxide radical, a polypropylene oxide chain, a tetramethylene oxide radical, and a polytetramethylene oxide chain.

It will obviously have been understood that for $R_5$, "radical" is referred to when m or n=1 and "chain" is referred to when m and n>1.

These monofunctional monomers can be obtained without any particular difficulty by condensation of an isocyanate-bearing unsaturated compound such as 3-isopropenyl-α, α-dimethylbenzylisocyanate (notably marketed under the reference m-TMI® by the company CYTEC) and of an amine-, hydroxyl-, thiol-, or epoxy-bearing compound which contains a flexible group ($R_5$). The reagents in question are:

firstly:

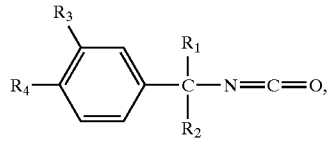

and secondly:

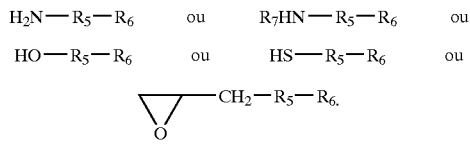

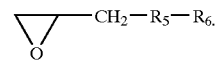

Some of said specific monofunctional monomers—those of formula (I) in which $R_5$ is selected from the group consisting in siloxane radicals, polysiloxane chains, carbonate radicals and carbonate chains—are new and constitute a further object of the present invention.

According to its first object, the present invention relates to radically polymerisable compositions which contain at least one monofunctional monomer as defined above and at least one monomer of an other type which is copolymerisable with said monofunctional monomer(s) and which is as defined below (one difunctional monomer).

The described monofunctional monomers are in fact comonomers of choice, which can improve the copolymerisation in question and which can confer the flexibility sought after to the copolymer resulting from the copolymerisation.

In order to make resins with very interesting optical and optionally photochromic properties (properties conjugated with satisfactory mechanical properties), the Applicant incorpores, as partners for copolymerisation:

at least one monofunctional monomer as defined above; and at least one difunctional monomer selected from the monomers of formulae (II) and (III) specified below. These are in fact diacrylate monomers, dimethacrylate monomers, even mixed acrylate and methacrylate monomers (reference is made to values of $R_1$ and $R'_1$ in said formulae (II) and (III)).

Such short chain difunctional monomers bring about rigidity to the final resin.

These difunctional monomers have already been described in the application WO-A-98 50443.

They are therefore of one or the other of formulae (II) and (III) below:

formula (II):

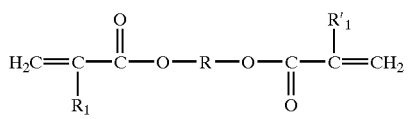

in which:

$R_1$ and $R'_1$, which are identical or different, independently are hydrogen or a methyl group;

R is an alkylene radical, which is linear or branched, and which comprises 2 to 8 carbon atoms, a cycloalkylene radical comprising 3 to 6 carbon atoms, an ether radical of formula (R'—O—R") in which R' and R", which are identical or different, independently are an alkylene radical, which is linear or branched, and which comprises 2 to 4 carbon atoms;

formula (III):

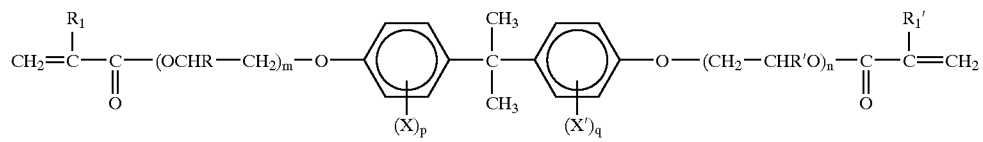

in which:

R₁, R'₁, R and R', which are identical or different, independently are hydrogen or a methyl group;

m and n are, independently, integers between 0 and 4 (inclusive); and are advantageously independently equal to 1 or 2;

X and X', which are identical or different, are a halogen and preferably represent chlorine and/or bromine; and p and q are, independently, integers between 0 and 4 (inclusive).

Said difunctional monomers which are incorporated in the compositions of the invention may or may not all be of the same formula (II) or (III). Thus, the polymerisable compositions of the invention can contain:

either difunctional monomers of a same formula (II);
or difunctional monomers of a same formula (III);
or mixtures (non-mixed) of different monomers of formula (II) or (III);
or mixtures (mixed) of monomers of formula(e) (II) and formula(e) (III).

According to a preferred variant of the invention, one or more symmetrical difunctional monomers of formula (III) are used.

Monomers of formula (II) or (III) are qualified as symmetrical, when R₁ and R'₁ groups are identical, the same applies for the R and R' groups, and the substituents X and X' for the compounds of formula (III).

Said symmetrical monomers of formula (III) are known and are available commercially or are easily accessible to the person skilled in the art. In fact, it may be noted that said monomers which do not possess a halogen on the aromatic rings correspond to the first monomers of formula (I) in the sense of document WO-A-92 05209. Said monomers of formula (III) having halogen(s) on the aromatic ring(s) are obtained easily by the person skilled in the art by using derivatives which are suitably substituted on said aromatic ring(s). Within the context of the invention, the monomers of formula (III), in which R and R', which are identical, are hydrogen or a methyl group, R₁ and R'₁ are a methyl group, m and n are independently equal to 1 or 2, and p=q=0, are preferred. A particularly advantageous variant corresponds to the monomer of formula (III) of the type above further with R=R'=H and m=n=2. Said monomer is marketed notably by the company AKZO NOBEL (NL) under the commercial denomination DIACRYL 121.

The synthesis of the asymmetrical monomers of formula (III) does not present any particular problem to the person skilled in the art.

The monomers of formula (II) are also well known and result from the classical reaction of an aliphatic diol and a short chain alkylene glycol (with a maximum of 8 carbon atoms in said chain) with at least one type of (meth)acrylic derivative depending on whether it is desired to obtain monomers of formula (II) which are symmetrical or asymmetrical at their ends.

The Applicant has obtained resins with interesting optical properties, and notably very efficient photochromic resins from mixtures of monomers of formulae:

(I)/(II)
(I)/(III)
(I)/(II)/(III).

Said photochromic resins have fading kinetics (return to the non-darkened state) which are particularly rapid.

It is not excluded that the compositions of the invention contain another copolymerisation partner which can confer flexibility to the final copolymer, and notably at least one difunctional monomer of formula (IV) (called long chain monomer):

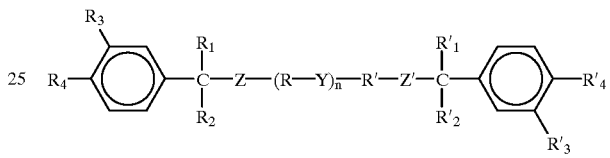

in which:

R₁, R'₁, R₂ and R'₂, which are identical or different, independently are hydrogen or an alkyl radical, which is linear or branched, advantageously linear, and which comprises 1 to 4 carbon atoms; and particularly advantageously corresponds to a methyl group;

R₃ and R₄, which are different, independently are one hydrogen and the other an alkenyl radical comprising 2 to 6 carbon atoms, advantageously 2 to 4 carbon atoms, and particularly advantageously an isopropenyl radical;

R'₃ and R'₄, which are different, independently are one hydrogen and the other an alkenyl radical comprising 2 to 6 carbon atoms, advantageously 2 to 4 carbon atoms, and particularly advantageously an isopropenyl radical; advantageously with R₃=R'₃ and R₄=R'₄;

Z represents a carbamate function (—NH—CO—O—), a thiocarbamate function (—NH—CO—S—), a urea function (—NH—CO—NH—) or an oxazolidone function

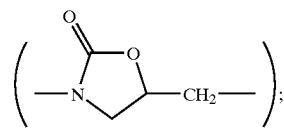

Z', independent of Z and advantageously respectively with respect to Z, represents a carbamate function (—O—CO—NH—), a thiocarbamate function (—S—CO—NH—), a urea function (—NH—CO—NH—) or an oxazolidone function

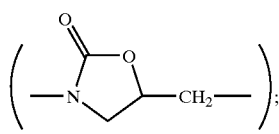

R' represents an alkylene radical, which is linear or branched, and which comprises 2 to 4 carbon atoms;

R, which is identical or different when n≧2, is an alkylene radical, which is linear or branched, and which comprises 2 to 4 carbon atoms;

Y, which is identical or different when n≧2, is oxygen or sulphur; and n is an integer defined such that the total number of carbon atoms, contained in the long chain situated between the two units Z and Z', be at least equal to 18 and advantageously be between 18 and 112 (inclusive).

This type of long chain difunctional monomer, of formula (IV), corresponds to the difunctional monomers of type (b), of formula (B), (B') and (B") of the document WO-A-98 50443. The teaching of document WO-A-98 50443 will be referred to for greater precision on this.

The polymerisable compositions of the invention can therefore contain difunctional monomers of said formula (IV) as monomers which can confer flexibility, in addition to the monofunctional monomers of formula (I).

The person skilled in the art, in view of the result sought after, will know how to optimise the relative proportions of the different types of monomers present.

The polymerisable compositions of the invention—jointly containing monomers of formula (I) and of formula (II) and/or (III)—can also further contain at least one aromatic monovinylic monomer of formula (C)

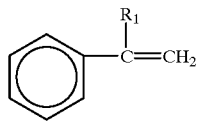

in which $R_1$=H or $CH_3$;
and/or
at least one aromatic divinylic monomer of formula (D):

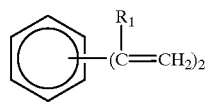

in which $R_1$=H or $CH_3$;
and/or
at least one (meth)acrylic monomer of formula (E):

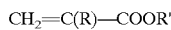

in which R=H or $CH_3$ and R' is a linear or branched alkyl radical having from 1 to 16 carbon atoms, an optionally substituted benzyl or phenoxy($C_1$–$C_4$)alkyl radical or a polyoxyethylene group of formula —$(CH_2$—$CH_2$—$O)_n$R" in which n is an integer between 1 and 10 and R"=$CH_3$ or $C_2H_5$;
and/or diallylphthalate,
and/or
at least one acrylic monomer having at least three reactive functions, advantageously selected from:
pentaerythritol triacrylate,
pentaerythritol tetraacrylate,
propoxylated glycerol triacrylate,
trimethylolpropane triacrylate,
polyurethane triacrylate,
dipentaerythritol hexaacrylate,
and preferably consisting of pentaerythritol triacrylate.

The vinylic monomers of formula (C)—styrene and/or methylstyrene—are advantageously incorporated in order to lower the viscosity of the mixtures of comonomers, to reduce the density of cross-linking, of the copolymer, and to adjust the refractive index of it.

The compounds of formula (D) consist of divinylbenzene (DVB) and di(isopropenyl)benzene. The incorporation of at least one compound of formula (D) can reveal to be advantageous notably in that said compound in general tempers the effects of the compound(s) of formula (C). The beneficial effect of such a compound of formula (D) has been notably demonstrated upon the expression of photochromic properties. In reference to divinylbenzene, insofar as this polymerised compound has a relatively high refractive index (n=1.61), its incorporation is equally beneficial in that it brings about an increase in the refractive index of the copolymers of the invention.

The polymerisable composition of the invention advantageously also contains at least one compound of formula (E). This is a (meth)acrylic monomer as defined above. Notably, it can be butyl, pentyl, hexyl, heptyl, octyl, 2-ethylhexyl, benzyl or phenoxyalkyl (meth)acrylate, or even ethyltriglycol(meth)acrylate. The presence of this type of compound can reveal to be advantageous for adjusting the viscosity of the mixture of comonomers, the density of cross-linking of the copolymer, the refractive index of said copolymer, for the turning out (from the mould) of said copolymer and for the implementation of finishing treatments of the latter.

The polymerisable composition can also contain diallylphthalate which notably enables the index and/or other optical and mechanical properties to be adjusted.

Finally, the polymerisable composition of the invention can advantageously further contain at least one acrylic monomer which has at least three reactive functions (which generally has 3, 4, 5 or 6 reactive functions). Such a monomer is incorporated as a monomer which constitutes the final matrix, but above all as a copolymerisation accelerator. Advantageously, it is selected from:
pentaerythritol triacrylate,
pentaerythritol tetraacrylate,
propoxylated glycerol triacrylate,
trimethylolpropane triacrylate,
polyurethane triacrylate,
dipentaerythritol hexaacrylate,
and preferably consists of pentaerythritol triacrylate.

Its incorporation, in substitution, at least partial, of a difunctional acrylic monomer or in addition to a suitable mixture of monomers improves the polymerisation kinetics, without inducing a fault in the final product.

Generally, said acrylic monomer(s), which is or are at least trifunctional and which is or are polymerisation accelerators, is or are incorporated at the rate of 2 to 10%, advantageously 4 to 6% by weight, with respect to the total weight of the mixture of monomers to be copolymerised.

As specified above, the incorporation of compounds of formula (C) and/or (D) and/or (E) and/or of diallylphthalate and/or of at least one acrylic monomer which is functionalised at least three times is not mandatory. The incorporation does however reveal to be generally advantageous.

The polymerisable compositions of the invention generally contain an effective amount of at least one radical polymerisation initiator, in addition to all the above compounds.

Said intervening radical polymerisation initiator(s) may be thermal or photochemical. Depending on the way the polymerisation—thermal polymerisation and/or photochemical polymerisation—is carried out, a single type of initiator (thermal or photochemical) is used or two types of initiators (thermal and photochemical) are used together.

Said intervening radical polymerisation initiator(s) must be "inert" towards the photochromic colorant(s) optionally present.

If a thermal polymerisation is carried out, the intervening radical polymerisation initiator(s) is (are) advantageously selected from the diazo compounds. These compounds are familiar to the person skilled in the art and are commercially available. Examples of such diazo compounds are 2,2'-azobisisobutyronitrile (AIBN), 2,2'-azobis(2-methylbutyronitrile)(AMBN) and 2,2'-azobis(2,4-dimethylpentanenitrile) (ADVN).

The thermal radical polymerisation initiator(s) is(are) used in an effective quantity, generally at a rate of 0.01 to 1% by weight, preferably from 0.05 to 0.5% by weight, with respect to the weight of the monomers present. In the absence of such an initiator or in the presence of too low an amount of it, it becomes necessary to carry out the copolymerisation at a higher temperature and this renders the reaction difficult to control. In the presence of too great an amount of such an initiator, an excess of free radicals may be generated, this excess of free radicals inducing a destruction of the photochromic colorant(s) optionally present and an accelerated fatigue of the final material. In this latter hypothesis, the reaction carried out may also accelerate and become difficult to control.

If a photochemical polymerisation is carried out, the intervening radical polymerisation initiator(s) is(are) especially selected from the acyl oxides and diacyl phosphine oxides. The said initiator advantageously consists in a diacyl phosphine oxide.

The photochemical radical polymerisation initiator(s) is(are) used in an effective quantity, generally at a rate inferior or equal to 2% by weight with respect to the weight of the monomers present.

If photochromic colorant(s) is (are) present, the said photochemical radical polymerisation initiator(s) is(are) generally used in a more limited quantity: less than or equal to 0.009 parts by weight per 100 parts by weight of the mixture of monomers to copolymerise (advantageously between 0.002 and 0.009 parts by weight). In such a context, the photochromic colorant(s) and the photochemical initiator(s) are generally competitors with regard the UV consumption. In such a context, the said photochemical radical polymerisation initiator(s) is(are) generally used in such a limited quantity, in combination with at least one thermal radical polymetrisation initiator. A thermal and photochemical polymerisation is then carried out.

It is however not totally excluded to use in such a context—presence of photochemical colorant(s)—greater amounts of photochemical initiator(s) if the above-explained competition due to the specific nature of the used colorant(s) and initiator(s) is minimized, even cancelled.

The man skilled in the art is able to determine and optimise the used amounts of radical polymerisation (thermal and/or photochemical) initiator(s).

In certain contexts, it can reveal to be advantageous, even indispensable, to further incorporate, within the polymerisable compositions of the invention, an effective amount (generally less than 5% by weight, in principle 0.01 to 2% by weight, with respect to the weight of monomers present) of at least one polymerisation modifier.

Obviously, it is necessary that said polymerisation modifier does not destroy the photochromic colorant(s) optionally present during the polymerisation and/or do not induce a discoloration of the material on its own. Said polymerisation modifier can be a non-halogenated chain transfer agent such as a linear alkane thiol or bis-mercapto-ethyl ether. Dodecanethiol may be cited as an example of a linear alkane thiol without being limiting. It is not excluded to use other types of chain transfer agents such as alkane thiols substituted with at least one aryl or alkyl radical or thiophenols. All these compounds are familiar to the person skilled in the art and are commercially available.

In the hypothesis in which it is desired to confer photochromic properties to the resins (copolymers) obtained by copolymerisation of the polymerisable compositions of the invention, said compositions can contain an effective amount of at least one photochromic colorant; said colorant(s) being advantageously selected from the group of spiroxazines, spiropyrans, chromenes, fulgides, fulgimides and mixtures thereof.

It is incidentally recalled at this juncture that it is not excluded to prepare photochromic resins by incorporating such photochromic colorants after the copolymerisation. Said colorants are then introduced by diffusion into the resin.

Very numerous photochromic colorants of the above type are described in the literature and are available on the market.

Spiroxazine colorants which may be used within the context of the present invention have notably been described in the patents U.S. Pat. Nos. 3,562,172, 4,634,767, 4,637, 968, 4,720,547, 4,756,973, 4,785,097, 4,792,224, 4,816,584, 4,831,142, 4,909,963, 4,931,219, 4,936,995, 4,986,934, 5,114,621, 5,139,707, 5,233,038, 4,215,010, 4,342,668, 4,699,473, 4,851,530, 4,913,544, 5,171,636, 5,180,524, 5,166,345, in the patent applications EP-A- 0 508 219, 0 232 295 and 0 171 909 and in the application FR-A-2 738 248.

Chromene colorants which are usable within the context of the present invention are notably described in patents U.S. Pat. Nos. 3,567,605, 4,889,413, 4,931,221, 4,980,089, 5,066,818, 5,106,998, 5,130,058, 5,200,116, 5,224,602, 5,238,981, 5,973,039, and the application EP-A-0 562 915. Said chromenes may notably consist of naphthopyrans.

Spiropyran colorants which are also usable within the context of the present invention are notably described in the following texts:

PHOTOCHROMISM G. Brown, Editor—Techniques of Chemistry—Wiley Interscience—Vol. III—1971—Chapter III—Pages 45–294—R. C. Bertelson.

PHOTOCHROMISM—Molecules & Systems—Edited by H. Dürr—H. Bouas-Laurent—Elsevier 1990—Chapter 8: Spiropyrans—Pages 314–455—R. Gugliemetti.

The incorporation of spiroxazines and/or chromenes is largely preferred within the context of the present invention.

It has been indicated that the compositions of the invention which are intended for generating a photochromic resin contain an effective amount of at least one photochromic colorant. It is in fact frequent, within the context of the present invention, to incorporate a combination of photochromic colorants, with the aim of obtaining a specific tint in the darkened state.

By way of reference and in no way limiting, it is indicated at this juncture that said photochromic colorants are generally incorporated in the compositions to be polymerised (and those which have been polymerised) of the invention at a rate of 0.01 to 1% by weight, advantageously at a rate of 0.05 to 0.5% by weight with respect to the total weight of monomers.

Said photochromic colorants may themselves very well contain a polymerisable and/or cross-linkable reactive group in their chemical formula as well. They are incorporated themselves then as co-monomers in the composition to be polymerised; and they are chemically bound, i.e. grafted to the matrix of said polymerised composition. Generally, the resins of the invention contain their photochromic colorant (s) free or bound to their matrix.

According to another of its objects, the invention relates to the copolymer (the resin) obtainable by conventional radical copolymerisation of the polymerisable composition of the invention. Said resin may or may not be endowed with photochromic properties. When at least one photochromic colorant is incorporated within it in order to provide it with such photochromic properties, it has been added prior to the copolymerisation into the polymerisable composition or after said copolymerisation (conventional introduction by diffusion in the resin).

Finally, a last object of the invention is constituted of photochromic or non-photochromic ophthalmic articles which are constituted wholly or in part of a resin of the invention. Non-limiting Examples of such articles are ophthalmic corrective lenses, solar lenses, glazings for vehicles or buildings . . . In these articles, the material, being optionally photochromic, of the invention may constitute the whole of the thickness of the article (mass article) or may only constitute a film or stratified layer applied on a support.

The invention will now be illustrated in a totally non-limiting way.

Examples 1 to 4 describe the synthesis of different monofunctional monomers of formula (I).

Examples 5 to 9 describe photochromic resin compositions which contain said monofunctional monomers and the method used for obtaining photochromic lenses from said resins.

Comparative Example 10 describes a resin composition which contains a dimethacrylate monomer (Diacryl 121) without any comonomer.

Comparative Example 11 describes a resin composition which contains a dimethacrylate monomer (Diacryl 121) with a styrenic compound.

Table 1 shows the half-time of fading and half-time of darkening as well as the optical quality obtained with the products of the Examples and Comparative Examples described.

EXAMPLE 1

0.4 mole of polyethylene glycol monomethyl ether Mn=350 (m=7) from ALDRICH and 0.06 g of dibutyltin dilaurate, as catalyst, are charged in a glass vessel equipped with a dropping funnel, with a stirrer and with a nitrogen purge.

The mixture is heated at 50° C. with stirring and nitrogen bubbling. 0.4 mole of m-TMI® (3-isopropenyl-α,α-dimethylbenzylisocyanate) from CYTEC is then added in 45 mn in using the dropping funnel (OH/NCO ratio=1).

After the addition of said M-TMI®, the mixture is heated at 60° C. for 1 h in order to complete the reaction.

The urethane monomer of the invention thus obtained is then cooled to ambient temperature and stored without any purification.

Said monomer is in the form of a colorless transparent liquid having a viscosity of 0.35 Pa.s at 20° C.

EXAMPLE 2

The same procedure as in Example 1 was repeated, except that the 0.4 mole of polyethylene glycol monomethyl ether 350 was replaced by 0.4 mole of triethylene glycol methyl ether ($M_w$=164; m=3) from ALDRICH.

The monomer obtained is a colorless transparent liquid having a viscosity of 0.37 Pa.s at 20° C.

EXAMPLE 3

The same procedure as in Example 1 was repeated, except that the 0.4 mole of polyethylene glycol monomethyl ether 350 was replaced by 0.4 mole of diethylene glycol monomethyl ether ($M_w$=120.15; m=2).

The monomer obtained is a colorless transparent liquid having a viscosity of about 0.46 Pa.s at 20° C.

EXAMPLE 4

The same procedure as in Example 1 was repeated, except that the 0.4 mole of polyethylene glycol monomethyl ether 350 was replaced by 0.4 mole of ethylene glycol monomethyl ether ($M_w$=76.1; m=1).

The monomer obtained is a colorless transparent liquid having a viscosity of about 0.29 Pa.s at 20° C.

EXAMPLE 5

20 g of the monomer of Example 1, 80 g of DIACRYL 121 (tetraethoxylated bisphenol A dimethacrylate) from AKZO, 0.5 g of 1-dodecyl mercaptan (NDM) used as chain transfer agent, 0.26 g of 2,2'-azobis(2,4-dimethylpentanenitrile)(ADVN) used as thermal initiator, 0.05 g of CR49 as photochromic dye (CR49=2-(p-dimethylaminophenyl)-2-(p-methoxyphenyl)-5-methyl-7,9-dimethoxy-[2H]naphtho[1,2-b]pyran, compound described in FR-A-2 751 648), and 0.009 g of IRGACURE 819 (bis(2,4,6-trimethylbenzoyl)phenylphosphine oxide) as photoinitiator, are mixed. The mixture is maintained at 25° C. by stirring up to the total dissolution of the compounds.

The mixture thus obtained is poured into lens mould type devices which are constituted of a mould and of a glass counter-mould having a curved edge of about 87 mm and a PVC gasket of 11 mm thickness.

The devices thus prepared are exposed to the light of fluorescent tubes (Brillant 840 from MAZDA) without UV filter, as described in the French patent application FR-A-2,783,829.

After gelation of the resin, the devices are placed in an oven and are subjected to the following cycle: rise from 25 to 50° C. in 5 h, and then from 50 to 95° C. in 3 h and finally a plateau at 95° C. for 2 h.

After a sufficient cooling, the samples are turned out of their moulds.

EXAMPLE 6

20 g of the monomer of Example 1, 80 g of DIACRYL 121 from AKZO, 0.9 g of NDM, 0.20 g of 2,2'-azobis(2-methylbutyronitrile) (AMBN), 0.05 g of CR49, are mixed. The mixture is maintained at 25° C. by stirring it up to the total dissolution of the compounds.

The mixture thus obtained is poured into lens moulds which are constituted of a mould and of a glass countermould having a curved edge of about 87 mm and a PVC gasket of 11 mm thickness.

The mixture is polymerised in the lens moulds for 16 h at 53° C., and then 2 h at 90° C.

After a sufficient cooling, the samples are turned out of their moulds.

EXAMPLE 7

The same procedure as in Example 5 was repeated, except that the 20 g of the monomer of Example 1 were replaced by 20 g of the monomer of Example 2.

EXAMPLE 8

The same procedure as in Example 5 was repeated, except that the 20 g of the monomer of Example 1 were replaced by 20 g of the monomer of Example 3.

EXAMPLE 9

The same procedure as in Example 5 was repeated, except that the 20 g of the monomer of Example 1 were replaced by 20 g of the monomer of Example 4.

COMPARATIVE EXAMPLE 10

The same procedure as in Example 5 was repeated, except that the Diacryl 121 was used alone, without other comonomers.

COMPARATIVE EXAMPLE 11

The same procedure as in Example 5 was repeated, except that the 20 g of the monomer of Example 1 were replaced by 20 g of styrene.

The optical quality was evaluated by visual inspection.

Lenses which were free from any defects were denoted <<+>>.

Lenses having some defects, such as flow lines or non-homogeneous parts, were denoted <<−>>.

The photochromic properties are evaluated by submitting the 2 mm thick lens, obtained by grinding and polishing, under UV light (xenon lamp) at room temperature until the coloration of the lens reaches the equilibrium. The coloration kinetics are recorded. The UV light is cut off and the fading kinetics are then recorded by measuring the transmission at 580 nm (λ max of the colored form of the photochromic molecule) versus time using a spectrophotometer HP 8452 from Hewlett Packard at 25° C.

The half-time of darkening and the half-time of fading are determined, denoted $t_{1/2}$ darkening and $t_{1/2}$ fading respectively. These parameters are familiar to the person skilled in the art. Their determination is based on the measurement of the optical densities of the lens:

optical density before exposure: $DO_0$, and optical density at the end of exposure: $DO_\infty$.

The half-time of darkening characterises the kinetics of coloration. It is the time necessary for obtaining a darkening which is half of the maximal darkening, the time necessary for obtaining an optical density equal to $$\frac{DO_\infty - DO_0}{2}.$$

The half-time of fading characterises the kinetics of return to the initial state (clear). At the end of the exposure, said exposure is cut off and the time necessary for a return of the optical density to the $$\frac{DO_\infty - DO_0}{2}$$

value is measured.

Table 1 shows said half-times of darkening and half-time of fading and the optical quality obtained with the products of the Examples and the Comparative Examples described.

The shore D hardness of the materials obtained is also indicated.

TABLE 1

|  | $t_{1/2}$ darkening (s) | $t_{1/2}$ fading (s) | Optical quality | Shore D hardness |
|---|---|---|---|---|
| Comparative Example |  |  |  |  |
| 10 | 24 | 64 | − | 88 |
| 11 | 112 | 800 | + | 89 |
| Example |  |  |  |  |
| 5 | 20 | 40 | + | 85 |
| 6 | 22 | 41 | + | 85 |
| 7 | 36 | 104 | + | 86 |
| 8 | 28 | 64 | + | 87 |
| 9 | 40 | 80 | + | 87 |

The examples above show that all the resin compositions of the invention give lenses having a good optical quality by comparison to that of Comparative Example 10.

Moreover, whatever the polyalkylene oxide chain or the alkylene oxide radical used for the synthesis of the monomer be, darkening and fading kinetics which are faster than those measured with the material obtained with the prior art styrenic monomer (Comparative Example 11), are observed with all the glasses made with the compositions of the invention.

What is claimed:

1. A radically polymerisable composition, characterised in that it comprises:
   (1) at least one monofunctional monomer having the formula (I) below:

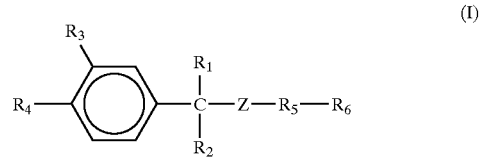

in which:
   $R_1$ and $R_2$, which are identical or different, independently are hydrogen or an alkyl radical, which is linear or branched and comprises 1 to 4 carbon atoms;
   $R_3$ and $R_4$, which are different, independently are one hydrogen and the other an alkenyl radical comprising 2 to 6 carbon atoms;
   Z represents a carbamate function (—NH—CO—O—), a thiocarbamate function (—NH—CO—S—), a urea function (—NH—CO—NR$_7$—, in which R$_7$ represents a hydrogen or a linear, branched or cyclic alkyl group which comprises 1 to 6 carbon atoms) or an oxazolidone function:

$$-\text{N}\underset{\underset{\text{O}}{\|}}{\overset{}{\bigcirc}}\text{CH}_2-;$$

R$_5$ is selected from the group consisting of:
(i) alkylene oxide radicals and polyalkylene oxide chains of formula:

$$-(\text{R}_7-\text{O})_m-$$

in which the R$_7$ groups, which are identical or different when m≧2, are alkylene radicals which are linear or branched and which comprise 2 to 5 carbon atoms, and in which m is an integer selected such that the total number of carbon atoms of $$-(\text{R}_7-\text{O})_m-$$

is between 2 and 112;
(ii) ester radicals and polyester chains of formula $$-(\text{R}_8-\underset{\underset{\text{O}}{\|}}{\text{C}}-\text{O})_n-$$

in which the R$_8$ groups, which are identical or different when n≧2, are alkylene radicals which are linear or branched and which comprise 2 to 5 carbon atoms, and in which n is an integer selected such that the total number of carbon atoms of $$-(\text{R}_8-\underset{\underset{\text{O}}{\|}}{\text{C}}-\text{O})_n-$$

is between 2 and 168;
(iii) siloxane radicals and polysiloxane chains of formula $$-(\underset{\underset{\text{R}_{10}}{|}}{\overset{\overset{\text{R}_9}{|}}{\text{Si}}}-\text{O})_o-$$

in which the R$_9$ and R$_{10}$ groups, which are independently identical or different when o≧2, are alkyl radicals which comprise 1 or 2 carbon atoms, and o is an integer between 1 and 18; and
(iv) carbonate radicals and polycarbonate chains of formula $$-(\text{R}_{10}{'}-\text{O}-\underset{\underset{\text{O}}{\|}}{\text{C}}-\text{O})_r-$$

in which the R$_{10}{'}$ groups, which are identical or different when r≧2, are alkylene radicals which are linear or branched and which comprise 1 to 5 carbon atoms, and in which r is an integer between 1 and 21; and R$_6$ is an alkyl radical or an aryl radical; and
(2) at least one difunctional monomer having the following formula (III), or a mixture of at least one difunctional monomer having formula (II) and at least one difunctinal monomer having formula (III), below:

(II)
$$\text{H}_2\text{C}=\underset{\underset{\text{R}_{11}}{|}}{\text{C}}-\underset{\underset{\text{O}}{\|}}{\text{C}}-\text{O}-\text{R}_{12}-\text{O}-\underset{\underset{\text{O}}{\|}}{\text{C}}-\underset{\underset{\text{R}'_{11}}{|}}{\text{C}}=\text{CH}_2$$

in which:

R$_{11}$ and R$_{11}{'}$, which are identical or different, independently are hydrogen or a methyl group;

R$_{12}$ is an alkylene radical which is linear or branched and which comprises 2 to 8 carbon atoms; a cycloalkylene radical comprising 3 to 6 carbon atoms; an ether radical of formula (R$_{13}$—O—R$_{13}{'}$) in which R$_{13}$ and R$_{13}{'}$, which are identical or different, independently are an alkylene radical which is linear or branched and which comprises 2 to 4 carbon atoms;

(III)

in which:

R$_{14}$, R$'_{14}$, R$_{15}$ and R$'_{15}$, which are identical or different, independently are hydrogen or a methyl group;

s and t are, independently, integers between 0 and 4 inclusive;

X and X', which are identical or different, are a halogen; and p and q are, independently, integers between 0 and 4 inclusive.

2. The composition according to claim 1, wherein said composition comprises at least one monofunctional monomer of formula (I) in which R$_3$ is an isopropenyl radical.

3. The composition according claim 1, wherein said composition comprises at least one monofunctional monomer of formula (I) in which R$_5$ represents an alkylene oxide radical or a polyalkylene oxide chain.

4. The composition according to claim 2, wherein said composition comprises at least one monofunctional monomer of formula (I) in which R$_5$ represents an alkylene oxide radical or a polyalkylene oxide chain.

5. A radically polymerisable composition, characterised in that it comprises:
(1) at least one monofunctional monomer having the formula (I) below:

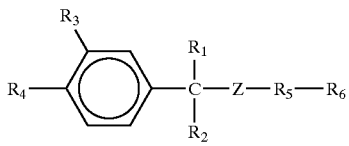 (I)

in which:

$R_1$ and $R_2$, which are identical or different, independently are hydrogen or an alkyl radical, which is linear or branched and comprises 1 to 4 carbon atoms;

$R_3$ and $R_4$, which are different, independently are one hydrogen and the other an alkenyl radical comprising 2 to 6 carbon atoms;

Z represents a carbamate function (—NH—CO—O—), a thiocarbamate function (—NH—CO—S—), a urea function (—NH—CO—NR$_7$—, in which R$_7$ represents a hydrogen or a linear, branched or cyclic alkyl group which comprises 1 to 6 carbon atoms) or an oxazolidone function:

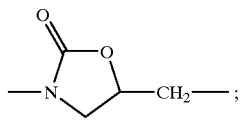

$R_5$ is selected from the group consisting of:
(i) alkylene oxide radicals and polyalkylene oxide chains of formula:

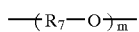

in which the $R_7$ groups, which are identical or different when m≧2, are alkylene radicals which are linear or branched and which comprise 2 to 5 carbon atoms, and in which m is an integer selected such that the total number of carbon atoms of

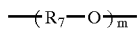

is between 2 and 112;
(ii) ester radicals and polyester chains of formula

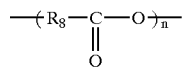

in which the $R_8$ groups, which are identical or different when n≧2, are alkylene radicals which are linear or branched and which comprise 2 to 5 carbon atoms, and in which n is an integer selected such that the total number of carbon atoms of

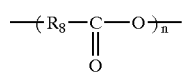

is between 2 and 168;
(iii) siloxane radicals and polysiloxane chains of formula

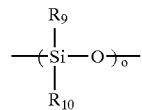

in which the $R_9$ and $R_{10}$ groups, which are independently identical or different when o≧2, are alkyl radicals which comprise 1 or 2 carbon atoms, and o is an integer between 1 and 18; and
(iv) carbonate radicals and polycarbonate chains of formula

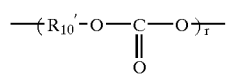

in which the $R_{10}'$ groups, which are identical or different when r≧2, are alkylene radicals which are linear or branched and which comprise 1 to 5 carbon atoms, and in which r is an integer between 1 and 21; and $R_6$ is an alkyl radical or an aryl radical; and (2) at least one difunctional monomer selected from those of formula (II) and formula (III) below:

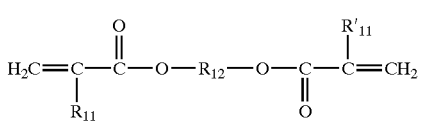 (II)

in which:

$R_{11}$ and $R_{11}'$, which are identical or different, independently are hydrogen or a methyl group;

$R_{12}$ is an alkylene radical which is linear or branched and which comprises 2 to 8 carbon atoms; a cycloalkylene radical comprising 3 to 6 carbon atoms; an ether radical of formula ($R_{13}$—O—$R_{13}'$) in which $R_{13}$ and $R_{13}'$, which are identical or different, independently are an alkylene radical which is linear or branched and which comprises 2 to 4 carbon atoms;

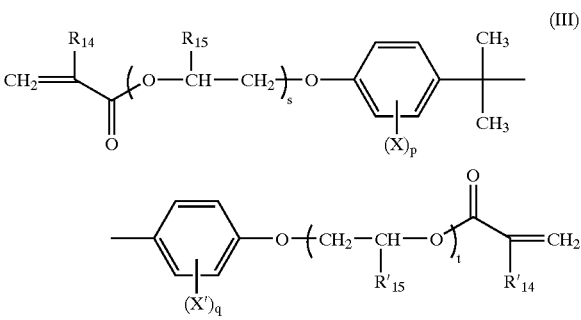 (III)

in which:

$R_{14}$, $R'_{14}$, $R_{15}$ and $R'_{15}$, which are identical or different, independently are hydrogen or a methyl group;

s and t are, independently, integers between 0 and 4 inclusive;

X and X', which are identical or different, are a halogen; and p and q are, independently, integers between 0 and 4 inclusive; and (3) at least one other difunctional monomer of formula (IV):

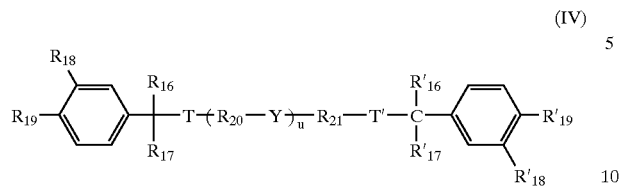
(IV)

in which:

R$_{16}$, R$_{17}$, R$_{16}$' and R$_{17}$', which are identical or different, independently are hydrogen or an alkyl radical which is linear or branched and comprises 1 to 4 carbon atoms;

R$_{18}$ and R$_{19}$, which are different, independently are one hydrogen and the other an alkenyl radical comprising 2 to 6 carbon atoms;

R$_{18}$' and R$_{19}$', which are different, independently are one hydrogen and the other an alkenyl radical comprising 2 to 6 carbon atoms;

T represents a carbamate function (—NH—CO—O—), a thiocarbamate function (—NH—CO—S—), a urea function (—NH—CO—NH—) or an oxazolidone function:

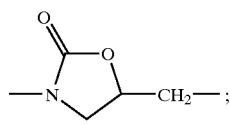

T', independent of T, represents a carbamate function (—O—CO—NH—), a thiocarbamate function (—S—CO—NH—), a urea function (—NH—CO—NH—) or an oxazolidone function:

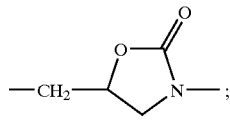

R$_{21}$ represents an alkylene radical, which is linear or branched and which comprises 2 to 4 carbon atoms;

R$_{20}$, which is identical or different when $u \geq 2$, is an alkylene radical which is linear or branched and which comprises 2 to 4 carbon atoms;

Y, which is identical or different when $u \geq 2$, is oxygen or sulphur; and u is an integer selected such that the total number of carbon atoms contained in the long chain situated between the two units T and T' is equal to at least 18.

6. The composition according to claim 5, wherein at least one of R$_{18}$, R$_{18}$', R$_{19}$ and R$_{19}$' is an isopropenyl radical.

7. The composition according to claim 5, wherein R$_{18}$=R$_{18}$' and R$_{19}$=R$_{19}$'.

8. The composition according to claim 5, wherein u is an integer selected such that the total number of carbon atoms contained in the long chain situated between the two units T and T' is between 18 and 112 inclusive.

9. The composition according to claim 2, wherein said composition further comprises at least one other difunctional monomer of formula (IV):

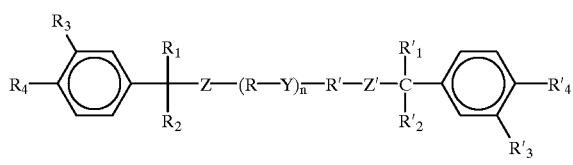
(IV)

in which:

R$_{16}$, R$_{17}$, R$_{16}$' and R$_{17}$', which are identical or different, independently are hydrogen or an alkyl radical which is linear or branched and which comprises 1 to 4 carbon atoms;

R$_{18}$ and R$_{19}$, which are different, independently are one hydrogen and the other an alkenyl radical comprising 2 to 6 carbon atoms;

R$_{18}$' and R$_{19}$', which are different, independently are one hydrogen and the other an alkenyl radical comprising 2 to 6 carbon atoms;

T represents a carbamate function (—NH—CO—O—), a thiocarbamate function (—NH—CO—S—), a urea function (—NH—CO—NH—) or an oxazolidone function:

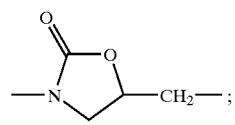

T', independent of T, represents a carbamate function (—O—CO—NH—), a thiocarbamate function (—S—CO—NH—), a urea function (—NH—CO—NH—) or an oxazolidone function:

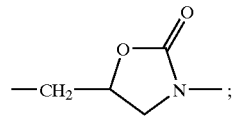

R$_{21}$ represents an alkylene radical, which is linear or branched and which comprises 2 to 4 carbon atoms;

R$_{20}$, which is identical or different when $u \geq 2$, is an alkylene radical which is linear or branched and which comprises 2 to 4 carbon atoms;

Y, which is identical or different when $u \geq 2$, is oxygen or sulphur; and u is an integer selected such that the total number of carbon atoms contained in the long chain situated between the two units T and T' is equal to at least 18.

10. The composition according to claim 3, wherein said composition further comprises at least one other difunctional monomer of formula (IV):

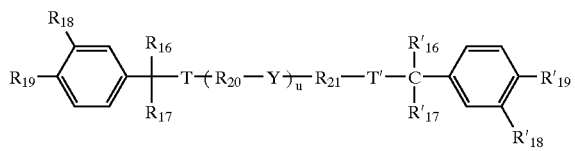
(IV)

in which:

$R_{16}$, $R_{17}$, $R_{16}'$ and $R_{17}'$, which are identical or different, independently are hydrogen or an alkyl radical which is linear or branched and which comprises 1 to 4 carbon atoms;

$R_{18}$ and $R_{19}$, which are different, independently are one hydrogen and the other an alkenyl radical comprising 2 to 6 carbon atoms;

$R_{18}'$ and $R_{19}'$, which are different, independently are one hydrogen and the other an alkenyl radical comprising 2 to 6 carbon atoms;

T represents a carbamate function (—NH—CO—O—), a thiocarbamate function (—NH—CO—S—), a urea function (—NH—CO—NH—) or an oxazolidone function:

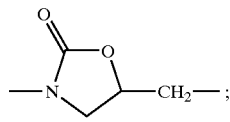

T', independent of T, represents a carbamate function (—O—CO—NH—), a thiocarbamate function (—S—CO—NH—), a urea function (—NH—CO—NH—) or an oxazolidone function:

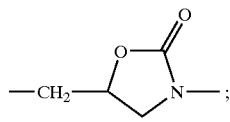

$R_{21}$ represents an alkylene radical, which is linear or branched and which comprises 2 to 4 carbon atoms;

$R_{20}$, which is identical or different when $u \geq 2$, is an alkylene radical which is linear or branched and which comprises 2 to 4 carbon atoms;

Y, which is identical or different when $u \geq 2$, is oxygen or sulphur; and u is an integer selected such that the total number of carbon atoms contained in the long chain situated between the two units T and T' is equal to at least 18.

11. The composition according to claim 4, wherein said composition further comprises at least one other difunctional monomer of formula (IV):

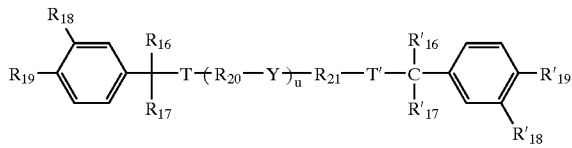
(IV)

in which:

$R_{16}$, $R_{17}$, $R_{16}'$ and $R_{17}'$, which are identical or different, independently are hydrogen or an alkyl radical which is linear or branched and which comprises 1 to 4 carbon atoms;

$R_{18}$ and $R_{19}$, which are different, independently are one hydrogen and the other an alkenyl radical comprising 2 to 6 carbon atoms;

$R_{18}'$ and $R_{19}'$, which are different, independently are one hydrogen and the other an alkenyl radical comprising 2 to 6 carbon atoms;

T represents a carbamate function (—NH—CO—O—), a thiocarbamate function (—NH—CO—S—), a urea function (—NH—CO—NH—) or an oxazolidone function:

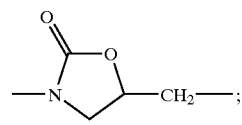

T', independent of T, represents a carbamate function (—O—CO—NH—), a thiocarbamate function (—S—CO—NH—), a urea function (—NH—CO—NH—) or an oxazolidone function:

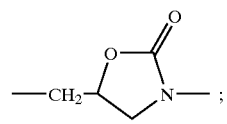

$R_{21}$ represents an alkylene radical, which is linear or branched and which comprises 2 to 4 carbon atoms;

$R_{20}$, which is identical or different when $u \geq 2$, is an alkylene radical which is linear or branched and which comprises 2 to 4 carbon atoms;

Y, which is identical or different when $u \geq 2$, is oxygen or sulphur; and u is an integer selected such that the total number of carbon atoms contained in the long chain situated between the two units T and T' is equal to at least 18.

12. The composition according to claim 1, wherein said composition further comprises:

(I) at least one aromatic monovinylic monomer of formula (C):

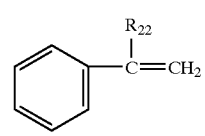
(C)

in which $R_{22}$=H or $CH_3$;

(II) at least one aromatic divinylic monomer of formula (D):

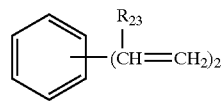
(D)

in which $R_{23}$=H or $CH_3$;

(III) at least one (meth)acrylic monomer of formula (E):

$CH_2=C(R_{24})-COOR_{25}$ (E)

in which $R_{24}$=H or $CH_3$ and $R_{25}$ is a linear or branched alkyl radical having from 1 to 16 carbon atoms, an optionally substituted benzyl or phenoxy($C_1$-$C_4$)alkyl radical or a polyoxyethylene group of formula $-(CH_2-CH_2-O)_v-R_{26}$ in which v is an integer between 1 and 10 and $R_{26}$=$CH_3$ or $C_2H_5$;

(IV) diallylphthalate;

(V) at least one acrylic monomer having at least three reactive functions; or (VI) combinations thereof.

13. The composition according to claim 12, wherein said at least one acrylic monomer having at least three reactive functions is selected from the group consisting of pentaerythritol triacrylate, pentaerythritol tetraacrylate, propoxylated glycerol triacrylate, trimethylolpropane triacrylate, polyurethane triacrylate, dipentaerythritol hexaacrylate, and combinations thereof.

14. The composition according to claim 2, wherein said composition further comprises:

(I) at least one aromatic monovinylic monomer of formula (C):

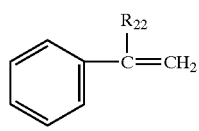

(C)

in which $R_{22}$=H or $CH_3$;

(II) at least one aromatic divinylic monomer of formula (D):

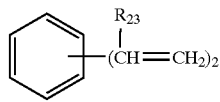

(D)

in which $R_{23}$=H or $CH_{23}$;

(III) at least one (meth)acrylic monomer of formula (E):

$CH_2=C(R_{24})-COOR_{25}$ (E)

in which $R_{24}$=H or $CH_3$ and $R_{25}$ is a linear or branched alkyl radical having from 1 to 16 carbon atoms, an optionally substituted benzyl or phenoxy($C_1$-$C_4$)alkyl radical or a polyoxyethylene group of formula $-(CH_2-CH_2-O)_v-R_{26}$ in which v is an integer between 1 and 10 and $R_{26}$=$CH_3$ or $C_2H_5$;

(IV) diallylphthalate;

(V) at least one acrylic monomer having at least three reactive functions; or (VI) combinations thereof.

15. The composition according to claim 3, wherein said composition further comprises:

(I) at least one aromatic monovinylic monomer of formula (C):

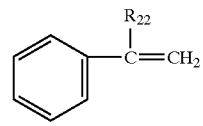

(C)

in which $R_{22}$=H or $CH_3$;

(II) at least one aromatic divinylic monomer of formula (D):

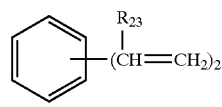

(D)

in which $R_{23}$=H or $CH_{23}$;

(III) at least one (meth)acrylic monomer of formula (E):

$CH_2=C(R_{24})-COOR_{25}$ (E)

in which $R_{24}$=H or $CH_3$ and $R_{25}$ is a linear or branched alkyl radical having from 1 to 16 carbon atoms, an optionally substituted benzyl or phenoxy($C_1$-$C_4$)alkyl radical or a polyoxyethylene group of formula $-(CH_2-CH_2-O)_v-R_{26}$ in which v is an integer between 1 and 10 and $R_{26}$=$CH_3$ or $C_2H_5$;

(IV) diallylphthalate;

(V) at least one acrylic monomer having at least three reactive functions; or (VI) combinations thereof.

16. The composition according to claim 4, wherein said composition further comprises:

(I) at least one aromatic monovinylic monomer of formula (C):

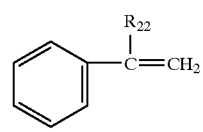

(C)

in which $R_{22}$=H or $CH_3$;

(II) at least one aromatic divinylic monomer of formula (D):

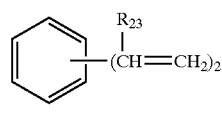

(D)

in which $R_{23}$=H or $CH_{23}$;

(III) at least one (meth)acrylic monomer of formula (E):

$CH_2=C(R_{24})-COOR_{25}$ (E)

in which $R_{24}$=H or $CH_3$ and $R_{25}$ is a linear or branched alkyl radical having from 1 to 16 carbon atoms, an optionally substituted benzyl or phenoxy($C_1$-$C_4$)alkyl radical or a polyoxyethylene group of formula $-(CH_2-CH_2-O)_v-R_{26}$ in which v is an integer between 1 and 10 and $R_{26}$=$CH_3$ or $C_2H_5$;

(IV) diallylphthalate;

(V) at least one acrylic monomer having at least three reactive functions; or (VI) combinations thereof.

17. The composition according to claim 5, wherein said composition further comprises:

(I) at least one aromatic monovinylic monomer of formula (C):

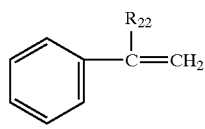

(C)

in which $R_{22}$=H or $CH_3$;

(II) at least one aromatic divinylic monomer of formula (D):

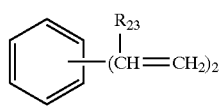

(D)

in which $R_{23}$=H or $CH_{23}$;

(III) at least one (meth)acrylic monomer of formula (E):

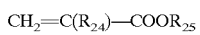

(E)

in which $R_{24}$=H or $CH_3$ and $R_{25}$ is a linear or branched alkyl radical having from 1 to 16 carbon atoms, an optionally substituted benzyl or phenoxy($C_1$–$C_4$)alkyl radical or a polyoxyethylene group of formula —($CH_2$—$CH_2$—O)$_v$—$R_{26}$ in which v is an integer between 1 and 10 and $R_{26}$=$CH_3$ or $C_2H_5$;

(IV) diallylphthalate;

(V) at least one acrylic monomer having at least three reactive functions; or (VI) combinations thereof.

18. The composition according to claim 9, wherein said composition further comprises:

(I) at least one aromatic monovinylic monomer of formula (C):

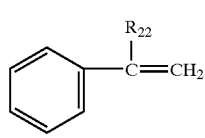

(C)

in which $R_{22}$=H or $CH_3$;

(II) at least one aromatic divinylic monomer of formula (D):

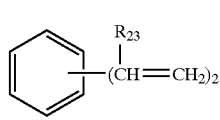

(D)

in which $R_{23}$=H or $CH_{23}$;

(III) at least one (meth)acrylic monomer of formula (E):

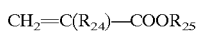

(E)

in which $R_{24}$=H or $CH_3$ and $R_{25}$ is a linear or branched alkyl radical having from 1 to 16 carbon atoms, an optionally substituted benzyl or phenoxy($C_1$–$C_4$)alkyl radical or a polyoxyethylene group of formula —($CH_2$—$CH_2$—O)$_v$—$R_{26}$ in which v is an integer between 1 and 10 and $R_{26}$=$CH_3$ or $C_2H_5$;

(IV) diallylphthalate;

(V) at least one acrylic monomer having at least three reactive functions; or (VI) combinations thereof.

19. The composition according to claim 10, wherein said composition further comprises:

(I) at least one aromatic monovinylic monomer of formula (C):

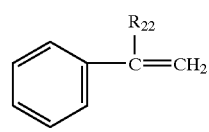

(C)

in which $R_{22}$=H or $CH_3$;

(II) at least one aromatic divinylic monomer of formula (D):

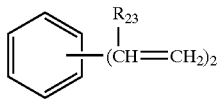

(D)

in which $R_{23}$=H or $CH_3$;

(III) at least one (meth)acrylic monomer of formula (E):

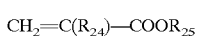

(E)

in which $R_{24}$=H or $CH_3$ and $R_{25}$ is a linear or branched alkyl radical having from 1 to 16 carbon atoms, an optionally substituted benzyl or phenoxy($C_1$–$C_4$)alkyl radical or a polyoxyethylene group of formula —($CH_2$—$CH_2$—O)$_v$—$R_{26}$ in which v is an integer between 1 and 10 and $R_{26}$=$CH_3$ or $C_2H_5$;

(IV) diallylphthalate;

(V) at least one acrylic monomer having at least three reactive functions; or (VI) combinations thereof.

20. The composition according to claim 11, wherein said composition further comprises:

(I) at least one aromatic monovinylic monomer of formula (C):

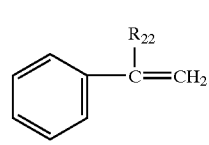

(C)

in which $R_{22}$=H or $CH_3$;

(II) at least one aromatic divinylic monomer of formula (D):

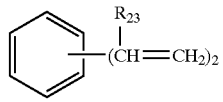

(D)

in which $R_{23}$=H or $CH_3$;

(III) at least one (meth)acrylic monomer of formula (E):

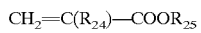

(E)

in which $R_{24}$=H or $CH_3$ and $R_{25}$ is a linear or branched alkyl radical having from 1 to 16 carbon atoms, an optionally substituted benzyl or phenoxy($C_1$–$C_4$)alkyl radical or a polyoxyethylene group of formula —($CH_2$—$CH_2$—O)$_v$— $R_{26}$ in which v is an integer between 1 and 10 and $R_{26}$=$CH_3$ or $C_2H_5$;

(IV) diallylphthalate;

(V) at least one acrylic monomer having at least three reactive functions; or (VI) combinations thereof.

21. The composition according to claim 1, wherein said composition further comprises an effective amount of at least one photochromic colorant which confers photochromic properties to said composition.

22. The composition according to claim 21, wherein said at least one photochromic colorant is selected from the group consisting of spiroxazines, spiropyrans, chromenes, fulgides, fulgimides, and combinations thereof.

23. The composition according to claim 2, wherein said composition further comprises an effective amount of at least one photochromic colorant which confers photochromic properties to said composition.

24. The composition according to claim 3, wherein said composition further comprises an effective amount of at least one photochromic colorant which confers photochromic properties to said composition.

25. The composition according to claim 5, wherein said composition further comprises an effective amount of at least one photochromic colorant which confers photochromic properties to said composition.

26. The composition according to claim 12, wherein said composition further comprises an effective amount of at least one photochromic colorant which confers photochromic properties to said composition.

27. A resin obtainable by radical copolymerisation of a polymerisable composition according to claim 1.

28. A resin obtainable by radical copolymerisation of a polymerisable composition according to claim 2.

29. A resin obtainable by radical copolymerisation of a polymerisable composition according to claim 3.

30. A resin obtainable by radical copolymerisation of a polymerisable composition according to claim 5.

31. A resin obtainable by radical copolymerisation of a polymerisable composition according to claim 12.

32. A resin obtainable by radical copolymerisation of a polymerisable composition according to claim 21.

33. An article which comprises a resin according to claim 27.

34. An article according to claim 33, wherein said article is an ophthalmic article.

35. An article which comprises a resin according to claim 28.

36. An article which comprises a resin according to claim 29.

37. An article which comprises a resin according to claim 30.

38. An article which comprises a resin according to claim 31.

39. An article which comprises a resin according to claim 32.

40. A monofunctional monomer having the formula (I) below:

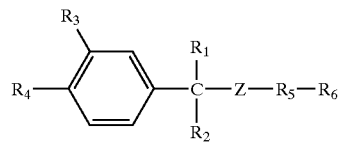

(I)

in which:

$R_1$ and $R_2$, which are identical or different, independently are hydrogen or an alkyl radical which is linear or branched and comprises 1 to 4 carbon atoms;

$R_3$ and $R_4$, which are different, independently are one hydrogen and the other an alkenyl radical comprising 2 to 6 carbon atoms;

Z represents a carbamate function (—NH—CO—O—), a thiocarbamate function (—NH—CO—S—), a urea function (—NH—CO—NR$_7$—, where $R_7$ represents a hydrogen or a linear, branched or cyclic alkyl group which comprises 1 to 6 carbon atoms) or an oxazolidone function:

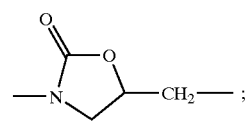

$R_5$ is selected from the group consisting of:

(A) siloxane radicals and polysiloxane chains of formula

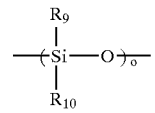

in which the $R_9$ and $R_{10}$ groups, which are independently identical or different when o≧2, are alkyl radicals which comprise 1 or 2 carbon atoms, and o is an integer between 1 and 18; and (B) carbonate radicals and polycarbonate chains of formula

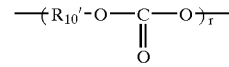

in which the $R_{10}'$ groups, which are identical or different when r≧2, are alkylene radicals which are linear or branched and which comprise 1 to 5 carbon atoms, and r is an integer between 1 and 21; and $R_6$ is an alkyl radical or an aryl radical.

41. The monomer according to claim 40, wherein $R_3$ is an isopropenyl radical.

42. A polymerisable composition comprising a monomer according to claim 40.

43. A resin obtainable by radical polymerisation of a polymerisable composition according to claim 42.

44. An article which comprises a resin according to claim 43.

45. An article according to claim 44, wherein said article is an ophthalmic article.

* * * * *